United States Patent [19]

Mattick et al.

[11] Patent Number: 5,288,617

[45] Date of Patent: Feb. 22, 1994

[54] METHOD OF PRODUCING AN ANTIGENIC PREPARATION

[75] Inventors: John S. Mattick; Belinda J. Anderson, both of Sydney; Thomas C. Elleman, Melbourne, all of Australia

[73] Assignees: Commonwealth Scientific and Industrial Research Organization, Campbell; University of Sydney, Sydney, both of Australia

[21] Appl. No.: 767,369

[22] Filed: Sep. 30, 1991

Related U.S. Application Data

[63] Continuation of Ser. No. 498,497, Mar. 26, 1990, abandoned, which is a continuation of Ser. No. 887,088, filed as PCT/AU85/00263, Oct. 31, 1985, published as WO86/02557, May 9, 1986, abandoned.

[30] Foreign Application Priority Data

Oct. 31, 1984 [AU] Australia ............... PG7930

[51] Int. Cl.$^5$ .................. C12P 21/00; C12N 15/00; C12N 1/21
[52] U.S. Cl. .................. 435/69.3; 435/172.3; 435/252.34
[58] Field of Search ............ 435/69.3, 71.2, 91, 435/170, 172.3, 252.2, 252.3, 320.1, 822, 848, 875, 252.34; 935/6, 11, 12, 22, 38, 39, 60, 63, 72; 424/88, 92

[56] References Cited

U.S. PATENT DOCUMENTS

| | | | |
|---|---|---|---|
| 4,696,896 | 9/1987 | Brinton | 435/7 |
| 4,769,240 | 9/1988 | Brinton | 424/92 |

FOREIGN PATENT DOCUMENTS

| | | | |
|---|---|---|---|
| 20662/83 | 10/1983 | Australia . | |
| 34979/84 | 11/1983 | Australia . | |
| 0049945A2 | 4/1982 | European Pat. Off. | G01N 33/54 |
| 0080806 | 6/1983 | European Pat. Off. | C12N 15/00 |
| WO85/05037 | 11/1985 | PCT Int'l Appl. | A61K 39/00 |
| 2094314A | 9/1982 | United Kingdom | C12N 15/00 |

OTHER PUBLICATIONS

*Biological Abstracts;* vol. 7(3); Feb. 1, 1984; 19281; Lee et al. 1983 Am. J. Vet. Res. 44(9):1676-81.
Elleman et al. 1984, FEBS Lett. 173(1):103-107.
Paranchych et al, Can. J. Microbiol. 25:1175-1181 (1979).
Froeholm et al. FEBS Lett. 73(1):29-32 (1977).
Elleman, T. C. et al. "Expression of Multiple Types . . . " Molecular Microbiology, 1987 1(3), 377-380.
Elleman, T. C. et al. "Isolation of the Gene . . . " Chemical Abstracts 101:145092v, vol. 101, 1984, p. 166.
Anderson, B. J. et al. "Cloning and Expression . . . " 3-Biochem Genetics 102:18866w, vol. 102, 1985, pp. 189-190.

*Primary Examiner*—Richard A. Schwartz
*Assistant Examiner*—Nancy Vogel
*Attorney, Agent, or Firm*—Nixon & Vanderhye

[57] ABSTRACT

Antigenic preparations active against species of bacteria naturally producing Type 4 fimbriae, such as *Bacteroides nodosus* which causes footrot in sheep, are produced by culturing a suitable genetically engineered aerobic or facultatively anaerobic host bacterial cell such as *Pseudomonas aeruginosa*. The host cell contains the gene encoding the fimbrial structural subunit antigens of at least one strain of the said species of bacteria and an endogenous compatible system for the morphogenetic assembly of Type 4 fimbriae and/or the genes for the morphogenetic assembly of such fimbriae derived from a Type 4 fimbriate species. The genetically engineered host cells are cultured such that nature fimbriae are produced as extracellular structures and the fimbriae are harvested, substantially free of the host cells, for use as the antigenic preparation. In preferred embodiments of the invention the natural fimbrial subunit gene is modified to enhance expression in the new host. Antigenic preparations according to this invention have proven to be effective vaccines against footrot.

26 Claims, 5 Drawing Sheets

```
AAAAAAAGCGCGTGTGCCAGAAAAATAATTTTTTAACTCATTGTTTTTAAATATAAAAAT
         10        20        30        40        50        60

AATGTTGGCATTGATGACGCATAATGAAAGGCATCAGGCAACTGACTCTAAACAAGATGA
         70        80        90       100       110       120

Dra I                              M  K  S  L  Q  K  G  F
TATTTAAATGTTCACATTCTTAATAGGAGAATATGATGAAAAGTTTACAAAAAGGTTTCA
        130       140       150       160       170       180

T  L  I  E  L  M  I  V  V  A  I  I  G  I  L  A  A  F  A  I
CCTTAATCGAACTCATGATTGTAGTTGCAATTATCGGTATCTTAGCGGCTTTCGCTATCC
        190       200       210       220       230       240

Pvu II
 P  A  Y  N  D  Y  I  A  R  S  Q  A  A  E  G  L  T  L  A  D
CTGCATATAACGACTACATCGCTCGTTCACAAGCAGCTGAAGGCTTAACATTGGCTGATG
        250       260       270       280       290       300

G  L  K  V  R  I  S  D  H  L  E  S  G  E  C  K  G  D  A  N
GTTTGAAGGTTCGCATTTCTGATCACTTAGAAAGCGGTGAATGTAAGGGAGATGCGAACC
        310       320       330       340       350       360

P  A  S  G  S  L  G  N  D  D  K  G  K  Y  A  L  A  T  I  D
CAGCTTCAGGATCTTTAGGTAATGATGATAAAGGTAAATACGCTCTTGCTACAATTGATG
        370       380       390       400       410       420

G  D  Y  N  K  D  A  K  T  A  D  E  K  N  G  C  K  V  V  I
GTGATTATAATAAAGACGCGAAAACTGCTGATGAGAAGAATGGTTGTAAAGTTGTAATCA
        430       440       450       460       470       480

Pst I
 T  Y  G  Q  G  T  A  G  E  K  I  S  K  L  I  V  G  K  K  L
CTTATGGTCAAGGTACTGCAGGCGAGAAAATTTCTAAGTTAATCGTTGGTAAGAAATTGG
        490       500       510       520       530       540

V  L  D  Q  F  V  N  G  S  Y  K  Y  N  E  G  E  T  D  L  E
TTTTAGATCAATTTGTTAATGGTTCATACAAATATAATGAAGGCGAAACTGATTTGGAAC
        550       560       570       580       590       600

L  K  F  I  P  N  A  V  K  N  *
TTAAATTTATTCCGAATGCTGTTAAAAACTAATAGCTAGCTCTTAAATGCGAAAGCCTCT
        610       620       630       640       650       660

Dra I
CTCTTGAGAGGCTTTTTTTATGGTTTATTGTTTCTATCATTTAAACAAAGGAAAATTAACT
        670       680       690       700       710       720

CATAATCATCTACTCTATATCTTGTCTAAGTAGG       Fig. 2
        730       740       750
```

Fig. 3
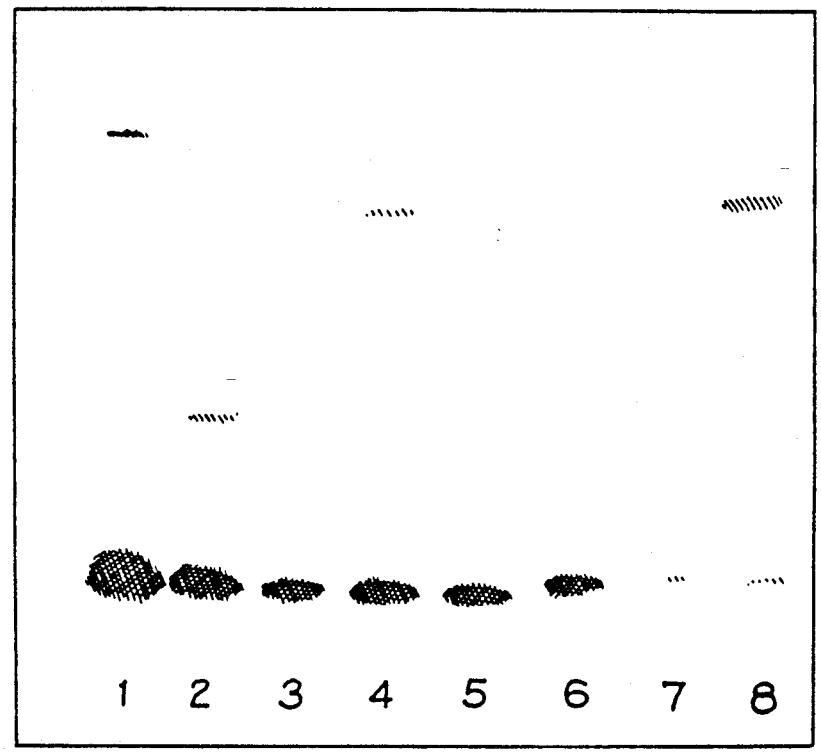
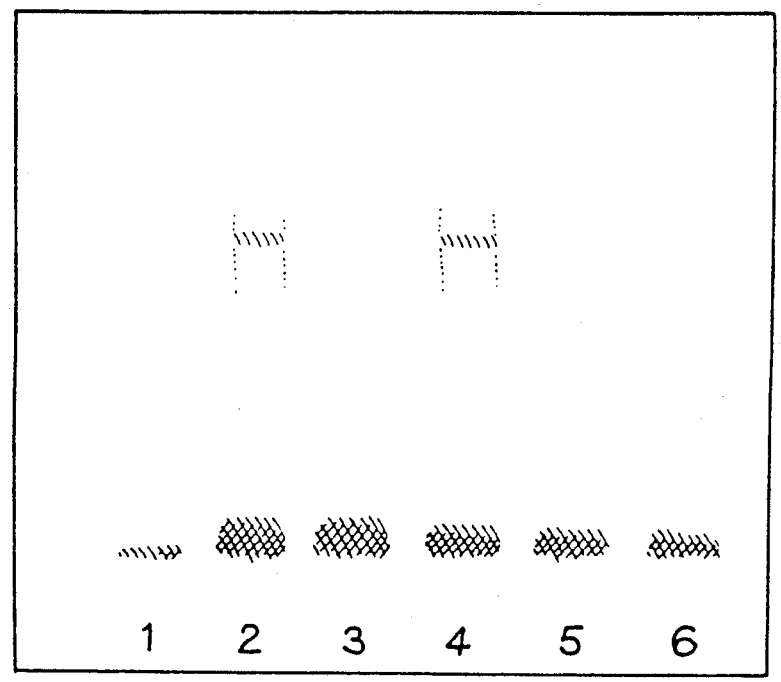
Fig. 4

METHOD OF PRODUCING AN ANTIGENIC PREPARATION

This is a continuation of application Ser. No. 07/498,497, filed Mar. 26, 1990, now abandoned, which is a continuation of application Ser. No. 06/887,088 filed as PCT/AU85/00263, Oct. 31, 1985, published as WO86/02557, May 9, 1986, now abandoned.

TECHNICAL FIELD

The present invention relates to a method of producing an antigenic preparation, capable of generating in vertebrates antibodies which will bind with Type 4 fimbrial antigens of bacterial pathogens, and to the antigenic preparation itself.

The specific example which will be used to illustrate this invention is that of the production of fimbrial antigens effective as a vaccine against *B.nodosus*, which is the essential causative agent of footrot infection in sheep and other ruminants.

BACKGROUND ART

*B.nodosus* is an anaerobic bacterium whose field isolates are characterized by the presence of surface filaments termed fimbriae (or common "Pili"), which are approximately 6 nm. in diameter and up to several hundred nm in length. In other bacteria, fimbriae have adhesive properties, and although the exact function of fimbriae in *B.nodosus* has not been clearly defined, it seems likely that they are involved in attachment to, and/or colonization of, epithelial tissues in the hoof. *B.nodosus* fimbriae have a polar location on the cell, and appear to be involved in surface translocation by a phenomenon known as twitching motility. Related fimbriae are found in a range of Gram-negative species classified within the genera *Pseudomonas, Neisseria, Moraxella, Acinetobacter, Bacteroides* and *Eikenella*, among others.

In the case of *B.nodosus*, a great deal of evidence has accumulated over the past decade to suggest that the fimbriae play a central role in both the infectivity of the bacteria and the protective immunological response of the sheep. Fimbriae are also implicated in pathogenesis and immunity in other bacterial pathogens. Vaccination of sheep with either whole cells or purified fimbriae from *B.nodosus* confers resistance to homologous footrot infections.

There are at least 8 or 9 major serogroups of *B.nodosus* (encompassing a number of subtypes), classified on the basis of the "K"-agglutination test.

The fimbriae have been shown to be the antigen involved in the specific agglutination reaction, and correspondingly the range of effective immunity conferred by vaccination with whole cells or fimbrial preparations is restricted to the serogroup/serotype involved.

The available commercial vaccines against footrot consist of a mixture of whole cells of different *B.nodosus* serotypes. However, the high cost of these vaccines, which is approximately an order of magnitude greater than that of other comparable vaccines (against e.g., the Clostridial group of infections), remains a serious obstacle to their widespread use and acceptance by the pastoral industry. As a result, present methods for the control of footrot continue to rely heavily on topical application of therapeutic agents, which have little or no impact on prevention of the disease.

The high cost of producing footrot vaccines is directly related to the difficulty of culturing fimbriate *B.nodosus*. This bacterium has very fastidious growth requirements, involving complex nutrient media and the absence of oxygen. Furthermore, since fimbrial expression is an unstable characteristic of *B.nodosus*, especially in the liquid broth culture conditions required for commercial production, batch-to-batch variation in the yields of fimbrial antigens may affect the quality and reliability of the vaccine preparations, introducing a significant cost burden in the area of quality control tests.

Applicants copending Australian patent application No. 34979/84 describes the production of the *B.nodosus* fimbrial subunit antigen expressed from cloned gene copies in *Echerichia coli*. The antigen is not assembled into mature fimbriae in these cells.

This invention describes the further development of this process, in that it describes the production of supramolecular, extracellular fimbrial structures from recombinant bacterial hosts. This provides substantial advantages in terms of both the antigenicity of the preparation (for vaccine purposes) and the practicalities and economics of antigen production. The invention makes use of a compatible fimbrial assembly system in a suitable Type 4 fimbrial host, such as *Pseudomonas aeruginosa*. This process is applicable to the production of fimbriae as vaccine antigens active against a variety of bacterial pathogens which produce Type 4 fimbriae.

DISCLOSURE OF THE INVENTION

The present invention consists in an antigenic preparation active against a species of bacteria naturally producing Type 4 fimbriae (as hereinafter defined), comprising mature fimbriae or parts derived therefrom representing at least one serotype of the said species of bacteria which have been produced by genetically engineered aerobic or facultatively anaerobic bacterial host cells containing the genes encoding the fimbrial structural subunit antigens of the said species of bacteria and an endogenous compatible system for the morphogenetic assembly of Type 4 fimbriae and/or those genes for the morphogenetic assembly of such fimbriae derived from a Type 4 fimbriate species.

The present invention further consists in a method for the preparation of an antigenic preparation active against a species of bacteria naturally producing Type 4 fimbriae as hereinafter defined, comprising culturing genetically engineered aerobic or facultatively anaerobic bacterial host cells, containing the genes encoding the fimbrial structural subunit antigens of at least one strain of the said species of bacteria and an endogenous compatible system for the morphogenetic assembly of Type 4 fimbriae and/or the genes for those morphogenetic assembly of such fimbriae derived from a Type 4 fimbriate species, such that mature fimbriae are produced as extracellular structures and harvesting the whole or a part of the fimbriae substantially free of the host cells.

*B.nodosus* fimbrial strands consist of a small repeated polypeptide subunit (protein) of approximately 150 amino-acids, of about 17,000 Daltons (17 kD) molecular weight, whose exact size appears to vary in different serotypes of the bacteria. Similar serological and structural variation occurs in the fimbrial subunits of other Type 4 fimbriate pathogens, such as *Neisseria gonorrhoeae, Neisseria meningitidis* and *Moraxella bovis*, presumably as a mechanism for evading host immune responses. We have found that fimbrial preparations derived from *B.nodosus* also contain another significant antigen, a protein of about 80,000 Daltons (80 kD) molecular weight. Our studies indicate that this protein is physically attached to the fimbrial strand, and may represent the basal protein which anchors the fimbriae to the surface of the bacterial cell. In *B.nodosus* this protein, like the fimbrial subunit, exhibits both structural and antigenic variation between different strains, and is another major polypeptide antigen to which sheep respond when infected with *B.nodosus*, or vaccinated with either whole cell or isolated fimbrial preparations.

We have found, using "Western" transfer matrix analyses, wherein fimbriae from a range of different *B.nodosus* isolates from different serotypes were displayed by gel electrophoresis, transferred to paper and challenged with a variety of homologous and heterologous antisera, that it is the fimbrial strand (i.e. the 17kD subunit antigen) which is the serogroup- and serotype-specific antigen, and therefore the primary protective antigen.

Applicants' copending Australian patent application No. 34979/84 describes the production of the structural subunit antigen of *B.nodosus* fimbriae from cloned gene copies expressed in *E.coli*. However, in this case the *B.nodosus* fimbrial subunit is not assembled into mature fimbrial structures on the cell surface, but rather is embedded in the membrane fraction of the cell. This has severe disadvantages in terms of both the antigenicity of the material and the difficulty of its isolation and purification, even though the level of expression of the protein may be increased by appropriate manipulation of the cloned gene. The present invention pertains to the further development of the vaccine, in that it describes the production of the specific active antigenic ingredient in the form of mature fimbrial structures from new genetically engineered bacterial host cells. The strategies and details of these constructions are described below.

The production of the antigen in the form of mature fimbriae has significant immunological and technical benefits with respect to the effectiveness of the vaccine, the simplicity of its components, and the ease and economics of its manufacture, based on the following considerations:

(i) Mature fimbriae appear to provoke a more intense and appropriate (i.e. K-agglutinating) immunological reaction than the equivalent dose of fimbrial subunit protein. A serological K-agglutination titre of about 5,000 is generally regarded as the minimum response commensurate with adequate protective immunity against infection with a given strain of *B.nodosus*. This level of response (and up to an order of magnitude higher) is readily achieved upon vaccination with mature fimbriae, but not with the isolated subunit protein, which elicits only poor levels of serum K-agglutinating antibodies.

(ii) The expression of mature fimbriae on the surface of the recombinant cell permits the simple and convenient separation on an industrial scale of the fimbrial antigens from the host bacterium. This has several advantages:

(a) Preparation of the antigen for use in an effective vaccine formulation does not require costly or complicated extraction or purification procedures, (b) The host cells may be removed from the vaccine preparation. This avoids potential problems associated with the use of recombinant organisms in vivo due to biosafety/biohazard considerations and/or the presence of toxic or other undesirable components in the host bacterium, (c) Removal of the host cells also eliminates the possibility of antigenic competition between cellular components and the fimbrial antigens, (d) The use of vaccines based on isolated fimbriae should reduce the incidence of necrotic reaction at the site of vaccination. This is a common problem with the presently available, whole cell, *B.nodosus* vaccines, especially when coupled with the use of strong immunological adjuvant conditions, such as oil emulsion and/or alum adsorption.

(e) The use of isolated fimbriae in vaccine formulations should simplify the standardization of ingredients and quality control, especially in the context of a multivalent vaccine, (iii) The expression of mature fimbriae in a recombinant host allows the possibility of incorporating more than one antigenic type of structural subunit into the actual strands produced. This would generate a simpler vaccine, with broad activity against more than one antigenic type, either with respect to the different serogroups of *B.nodosus*, or as a mixed vaccine active against Type 4 fimbrial antigens from more than one pathogenic species.

The biosynthesis and assembly of fimbrial strands i.e. morphogenetic expression, appears to require the participation of several genes, apart from that encoding the structural subunit itself. For example, studies of the plasmid and chromosomal encoded Type 1 or Type 2 fimbrial systems of uropathogenic and enterotoxigenic strains of *E.coli* have shown that there are at least five to seven genes involved in the process - one codes for the fimbrial subunit, another for a basal protein, and the remainder for other polypeptides whose exact roles are not clearly understood, but which appear to function as assembly factors in the construction and extrusion of the fimbrial strand. These genes are normally clustered in the genome, and occupy up to 5 to 10 kilobases (kb) of DNA sequence information.

The gene encoding the 17kD structural subunit of the *B.nodosus* serotype A1 fimbria is located within a 5.5 kb Hind III segment of *B.nodosus* DNA, cloned into an *E.coli* plasmid vector, as described in our co-pending Australian patent application No. 34979/84. The gene is expressed in *E.coli* from a promoter within the cloned sequence. This gene is representative of those found in other serotypes of *B.nodosus*, as well as in other Type 4 fimbriate bacteria. In this context, we have also successfully cloned, using the same general strategies, the genes encoding the structural subunits of *Pseudomonas aeruginosa* strain PAK fimbriae, and those of a number of different serotypes of *B.nodosus*, although, in the latter cases at least, there is evidently some degree of restriction site polymorphism and sequence divergence between the different serotypes. For example, the gene encoding the structural subunit of *B.nodosus* serogroup C fimbriae is located within a cloned (Hind III) fragment of about 4.5 kb, which itself contains two additional internal Hind III sites, at least one of which appears to lie within the functional gene. The serogroup F fimbrial subunit gene is located within a cloned Hind III fragment of about 3 kb. In no case, however, have we yet observed the formation of mature fimbrial structures on the surface of recombinant *E.coli* host cells expressing these cloned genes. These clones also do not appear to express the basal protein antigen. The probable reason for the lack of assembly of mature fimbriae in the recombinant cells is that the cloned DNA segments do not include all of the information required for proper morphogenetic expression i.e. some or all of the genes coding for the basal protein and assembly factors and/or associated promoters. Alternatively, some or all of these additional genes may not express or function properly in the E.coli host cell environment.

The problem of obtaining morphogenetic expression of fimbriae in recombinant hosts may be approached by attempting to clone and express the other genes required. The initial strategy here involves extension of the cloned sequences flanking the structural subunit qene, on the assumption that the genes are in fact clustered as in E.coli, by chromosome "walking" using a series of overlapping clones generated by digestion with different restriction endonucleases (with 6 base recognition sequences) or by partial digestion with a restriction enzyme such as Sau 3A (which has a 4-base recognition sequence). Low copy number vectors may be required to avoid deleterious gene dosage effects associated with the expression of membrane proteins, and we have evidence to suggest that such genes may be located in the vicinity of the B.nodosus fimbrial subunit genes, which has caused problems in the cloning of these sequences. However, once obtained an extended region around the subunit gene may be reconstructed and tested in a range of bacterial hosts for the ability to produce mature fimbrial structures, assessed using standard techniques for isolating fimbriae, immunological and electrophoretic analyses, and electron microscopic examination of whole cells and derived fractions. An alternative strategy is to use transposon mutagenesis to generate a series of fim⁻ mutants, and to clone those genes affected using the transposon as a genetic or hybridization marker. This strategy does not require that the genes be clustered in the bacterial genome. The genes involved (in either case) may be reconstructed into a functional system incorporating the fimbrial subunit, with appropriate molecular genetic manipulation, as required, to maximize and stabilize fimbrial biosynthesis, and to provide the appropriate balance of expression of each of the genes involved.

The problem of morphogenetic expression of fimbriae may also be approached by genetic or molecular genetic complementation of the fimbrial subunit gene with a compatible assembly system derived in whole or part from other bacteria. Although this approach may involve gene isolation and/or modification as outlined above, it has the advantage that it potentially provides the simplest solution to the problem. Attempts to complement missing functions by subcloning the B.nodosus fimbrial subunit gene into plasmid vectors containing E.coli fimbrial assembly genes have thus far been unsuccessful, as have similar experiments carried out with the N.gonorrhoeae fimbrial subunit gene, whereas Klebsiella pneumonias fimbriae have been expressed from cloned DNA segments inserted into both E.coli and Salmonella typhimurium. These results suggest that some basic incompatibility does exist between Type 4 fimbriae and those systems found in fimbriate Enterobacteriaceae which includes the genera Klebsiella, Escherichia and Salmonella. There are in fact considerable differences between the structural subunits of Type 4 fimbriae and those found in E.coli, especially with respect to the location of hydrophobic regions, which occur at the N-terminus in the former and at the C-terminus in the latter. On the other hand, there are striking similarities between the fimbrial subunits from different Type 4 fimbriate bacteria, including Bacteroides nodosus, Pseudomonas aeruginosa, Neisseria gonorrhoeae, Neisseria meningitidis, Moraxella nonliquefaciens and Moraxella bovis (see Table 1), which are the only species for which detailed data are currently available. Sequence analyses have shown that the fimbrial subunits of these bacteria all share the distinctive feature of having the unusual amino-acid, methylphenylalanine (Me-Phe), as the first residue in the mature protein. These fimbrial subunits also share a very high degree of amino-acid sequence homology throughout the first 20 to 25% of the protein, even to the extent that where changes have occurred, these generally involve conservative amino-acid substitutions. The total length of these proteins varies in the range of approximately 140 to 160 amino-acids. Strong homology is observed within the first 32 residues with further pockets of homology extending up to about residue 50. In addition, the subunits also seem to share a similar and unusual 6 to 7 amino-acid positively-charged N-terminal leader sequence in the primary translation product, which is cleaved from the protein at some stage prior to incorporation into the mature fimbrial strand. Interspecies variation between these fimbrial subunits occurs primarily within the carboxy-terminal two-thirds of the protein. Intraspecific variation (i.e. between different serotypes) also occurs in this region, and involves not only amino-acid substitutions, but also small in frame insertions and deletions.

TABLE 1

Comparison of the N-terminal amino-acid sequences of the fimbrial subunits of B. nodosus (1), P. aeruginosa (2), N. gonorrhoeae (3), N. meningitidis (4), M. nonliquefaciens (5) and M. bovis (6).

|   |   |   |   |   |   |   | 1 |     |   |   |   | 10 |   |   |   |   |   |   |   | 20 |
|---|---|---|---|---|---|---|---|-----|---|---|---|----|---|---|---|---|---|---|---|----|
| 1. | M | K | S | L | Q | K | G | MeF | T | L | I | E  | L | M | I | V | V | A | I | I | G | I | L | A | A | F | A |
| 2. | M | K | — | A | Q | K | G | MeF | T | L | I | E  | L | M | I | V | V | A | I | I | G | I | L | A | A | I | A |
| 3. | M | N | T | L | Q | K | G | MeF | T | L | I | E  | L | M | I | V | I | A | I | V | G | I | L | A | A | V | A |
| 4. |   |   |   |   |   |   |   | MeF | T | L | I | E  | L | M | I | V | V | A | I | V | G | I | L | A | A | V | A |
| 5. |   |   |   |   |   |   |   | MeF | T | L | I | E  | L | M | I | V | I | A | I | I | G | I | L | A | A | I | A |
| 6. | M | N | — | A | Q | K | G | MeF | T | L | I | E  | L | M | I | V | I | A | I | I | G | I | L | A | A | I | A |

|   |   |   |   |   |   | 30 |   |   |   |   |   |   | 40 |   |   |   |   |   |   |   |
|---|---|---|---|---|---|----|---|---|---|---|---|---|----|---|---|---|---|---|---|---|
| 1.I | P | A | Y | N | D | Y | I | A | R | S | Q | A | A | E | G | L | T | L | A | L | A | D | G | L | K | V | R ... |
| 2.I | P | Q | Y | Q | N | Y | V | A | R | S | E | G | A | S | A | L | A | S | V | N | P | L | K | T | T | V | E ... |
| 3.L | P | A | Y | Q | D | Y | T | A | R | A | Q | V | S | E | A | I | L | L | A | E | G | Q | K | S | A | V | T ... |
| 4.L | P | A | Y | Q | D | Y | E | S | R | A | Q | M | S | E | A | L | I | L | A | E | G | Q | K | T | A | V | V ... |
| 5.L | P | A | Y | Q | D | Y | I | A | R | A | Q | V | S | E | A | F | T | L | A | D | G | L | K | T | G | I | S ... |
| 6.L | P | A | Y | Q | D | Y | I | S | K | S | Q | T | T | R | V | V | G | E | L | A | A | G | K | T | A | V | D ... |

Legend:
The first 48 residues of the mature fimbrial subunit are shown, numbered from the N-terminal

TABLE 1-continued methylphenylaline (MeF) residue, as well as the leader sequence present in the primary translation product (where this has been determined). The arrow (⟶) indicates the point of cleavage, although in a proportion of molecules cleavage apprear to occur on the carboxy-terminal side of the MeF residue (--⟶). Dashes indicated the absence of a residue at the point. Residues are listed using the one letter code for amino-acids suggested by the IUPAC-IUB Commission on Biochemical Nomenclature.

---

In *N.gonorrhoeae* it has been suggested that the conserved amino-terminal portion of the fimbrial subunit is involved in subunit-subunit interaction within the fimbrial strand, and this may well be the case. However, we reasoned that the strong conservation of this sequence across a range of different bacterial species and genera which possess Type 4 fimbriae has occurred because this amino-terminal region contains important topogenic signals for fimbrial morphogenesis, in terms of the interaction of the structural subunit with the assembly system, factors and pathway involved. If so, the fimbrial subunits containing these signals should function interchangeably throughout the Type 4 (MePhe) group. This is the essence of the invention, which we have now demonstrated by the morphogenetic expression and production of *B.nodosus*-type fimbriae from a cloned subunit gene inserted into fimbriate *P.aeruginosa,* and the use of this material as an effective vaccine against footrot in sheep. *P.aeruginosa* was selected (from among the available Type 4 fimbriate bacteria) as the (prototype) recipient host, on the basis that this species is a genetically well-characterized aerobe, which is easily cultured on relatively simple media, and for which plasmid shuttle vector systems are available for gene cloning and transfer.

Type 4 fimbriae are herein defined as those fimbriae which (i) are commonly found in bacterial species exhibiting the phenomenon known as twitching motility, although this may not always be present (see below); (ii) have a polar or polar-like location on the surface of the cell; and (iii) possess a highly conserved sequence in the amino-terminal region of the structural subunit viz. (a) a similar short (6 to 7 amino-acid) leader sequence in the primary translation product, followed by (b) a hydrophobic region showing (greater than 75%) homology with the following 32 amino-acid consensus sequence, beginning with the (modified) phenylalanine residue normally found in position 1 of the mature protein:

MeF T L I E L M I V (I/V) A I (I/V) G I L A A (I/V)
A (I/L) P A Y (Q/N) D Y (I/V) (A/S) (R/K) (A/S) Q.
(see FIG. 1)

The brackets indicate that either one of the enclosed residues may be present at that position. These pairs are conservative, in the sense that each of the amino-acids in the pair has a similar structure and properties e.g. isoleucine/valine (I/V), isoleucine/leucine (I/L), glutamine/asparagine (Q/N), arginine/lysine (R/K), and to a lesser extent, alanine/serine (A/S).

It should be noted that while twitching motility is usually exhibited by strains containing Type 4 fimbriae, this is not always or necessarily the case. For example, some (mutant) strains of *P.aeruginosa* have been shown to retain polar Type 4 fimbriae even though they have apparently lost the ability to exhibit twitching motility. Type 4 fimbriae are found in *B.nodosus, P.aeruginosa, N.gonorrhoeae, N. meningitidis, M.nonliquefaciens* and *M.bovis,* and probably also in *Acinetobacter calcoaceticus, Bacteroides ureolyticus, Eikenella corrodens, Moraxella kingae, Moraxella lacunata, Moraxella osloensis, Pseudomonas acidovorans, Pseudomonas alcaligenes, Pseudomonas maltophilia, Psuedomonas pseudoalcaligenes, Pseudomonas putrefaciens, Pseudomonas solanacearum, Pseudomonas stutzeri* and *Pseudomonas testosteroni,* among others. Type 4 fimbriae may possibly also be found in some Gram-positive species such as *Steptococcus sanguis.*

The activity of the antigenic preparation may be exhibited as the ability to generate antibodies or some other immune response in vivo against the said species of bacteria and/or ability to bind antibodies against the bacteria. Thus the antigenic preparation may be useful either as a vaccine or as a diagnostic test for the said bacteria or its antibodies.

The source of the fimbrial subunit gene may be any species or strain thereof which possess Type 4 fimbriae. There may be present in the host organism the fimbrial subunit gene from a number of different Type 4 fimbriate bacteria. In preferred embodiments of the invention the host organism contains the fimbrial subunit genes for a number of serotypes of a single Type 4 fimbriate species.

The host cell may be any compatible species or strain which expresses Type 4 fimbriae and which is preferably an aerobe or facultative anerobe capable of being transformed with and maintaining a suitable plasmid vector coding at least for the fimbrial subunit gene. The host cell may contain the exogenous genes either in a plasmid or by insertion into its chromosome. The plasmid may be either exogenous or endogenous.

In preferred embodiments of the invention the genes for the morphogenetic assembly of the fimbriae are endogenous to the host cell which is itself of a Type 4 fimbriate species. In other embodiments of the invention, however, the genes may be exogenous, being derived from the same species as the subunit genes or from another Type 4 fimbriate species.

In a preferred embodiment a promoter is employed to increase the level of gene expression and may be any promoter active in the host species, with or without accompanying regulatory sequences. Preferred promoters include the $P_L$ and $P_R$ promoters from the bacteriophage lambda, as well as other strong natural or synthetic promoters, such as the hybrid tac promoter. Regulation of the promoter may be of a chemical or physical nature as is well known in the art. In an alternative embodiment of the invention the molecular structure of the subunit gene may be altered, particularly to render its leader sequence more homologous to that of the host cell, so as to enhance morphogenetic expression in a particular host.

The antigenic preparations are preferably administered with a conventional adjuvant and carrier system when used as a vaccine.

BRIEF DESCRIPTION OF THE DRAWINGS

The following example is described with reference to the accompanying drawings in which:

FIG. 2 shows the nucleotide sequence of the gene encoding the fimbrial subunit of B.nodosus VCS 1001 and flanking DNA. The derived amino-acid sequence of the fimbrial subunit is shown using the standard one letter code suggested by IUPAC-IUB Commission on Biochemical Nomenclature. The positions of the Dra 1 restriction endonuclease sites (TTTAAA) flanking the gene, and the Pvu II (CAGCTG) and Pst 1 (CTGCAG) sites within the gene are indicated by the lines.

FIG. 3 shows a Western transfer analysis of cell pellet and supernatant fractions of P.aeruginosa PAK/2Pfs and E.coli E418 cells containing pJSM202. Recombinant cells were grown on Luria broth agar medium containing the appropriate antibiotic. P.aeruginosa cells were cultured overnight at 37° C. E.coli cells were cultured for 8 hours at 30° C., then shifted to 42° C. for 4 hours to induce the synthesis of the fimbrial subunit from the (derepressed) $P_L$ promoter. Cells were harvested in phosphate-buffered saline (PBS), subjected to mechanical blending, and the cells pelleted by centrifugation. The supernatant was then removed and the cells resuspended in fresh PBS. Equal amounts of cell and supernatant fractions were then subjected to electrophoresis on SDS-urea-8 to 15% gradient polyacrylamide gels in a standard tris-glycine (Laemmli) buffer system. The resulting gel displays were then electrophoretically transferred to nitrocellulose paper, incubated with anti-B.nodosus fimbrial antiserum and then with $^{125}$I-labelled Protein A, under standard conditions. The position of bound antibodies was visualized by autoradiography. Lanes 2, 4, 6 and 8 contain cell pellet material. Lanes 3, 5 and 7 contain supernatant fractions. Lanes 2 and 3, 4 and 5 are derived from two independent primary clones of P.aeruginosa PAK/2Pfs transformed with pJSM202. Lanes 6 and 7 are derived from E.coli E418 carrying pJSM202. Lane 8 contains P.aeruginosa PAK/2Pfs cells carrying pJSM125. Lane 1 contains purified fimbriae from B.nodosus VCS 1001.

FIG. 4 shows the results of the purification of fimbriae from P.aeruginosa PKN-Al. Cells were cultured on agar plates as described in the text, and harvested in phosphate-buffered saline (PBS). The cells were removed by centrifugation and the supernatant reserved (supernatant fraction). The cells were then resuspended in PBS, subjected to mechanical blending, and again the cells removed by centrifugation, to yield a blended supernatant fraction. The supernatant and blended supernatant fractions were then divided equally and subjected to either isoelectric precipitation at pH 4.5 or precipitation with 0.1M $MgCl_2$. The precipitates were recovered by centrifugation, redissolved in PBS and analysed by SDS - polyacrylamide gel electrophoresis, as described in the legend to FIG. 3. Protein bands were visualized by staining with Coomassie Blue R250. Lanes 2 and 3 contain fimbriae recovered from the supernatant fraction by isoelectric or $MgCl_2$ precipitation, respectively. Lanes 4 and 5 contain fimbriae recovered from the blended supernatant fraction by isoelectric or $MgCl_2$ precipitation, respectively. Lanes 2 to 5 all contain an amount of material equivalent to 3.5% of that recovered from a single Petri dish culture of PKN-Al cells. Lane 1 contains fimbriae purified from P.aeruginosa PAK/2Pfs (about 5 ug). Lane 6 contains fimbriae purified from B.nodosus VCS 1001 (about 10 ug).

BEST MODE OF CARRYING OUT THE INVENTION

EXAMPLE

The specific example used to illustrate this invention involves the morphogenetic expression of *B.nodosus* fimbriae from a cloned subunit gene inserted, after appropriate genetic engineering manipulations, into a fimbriate strain of *Pseudomonas aeruginosa,* and the use of fimbrial preparations derived therefrom as an effective vaccine against footrot infection in sheep caused by the homologous *B.nodosus* strain.

Figure 1:
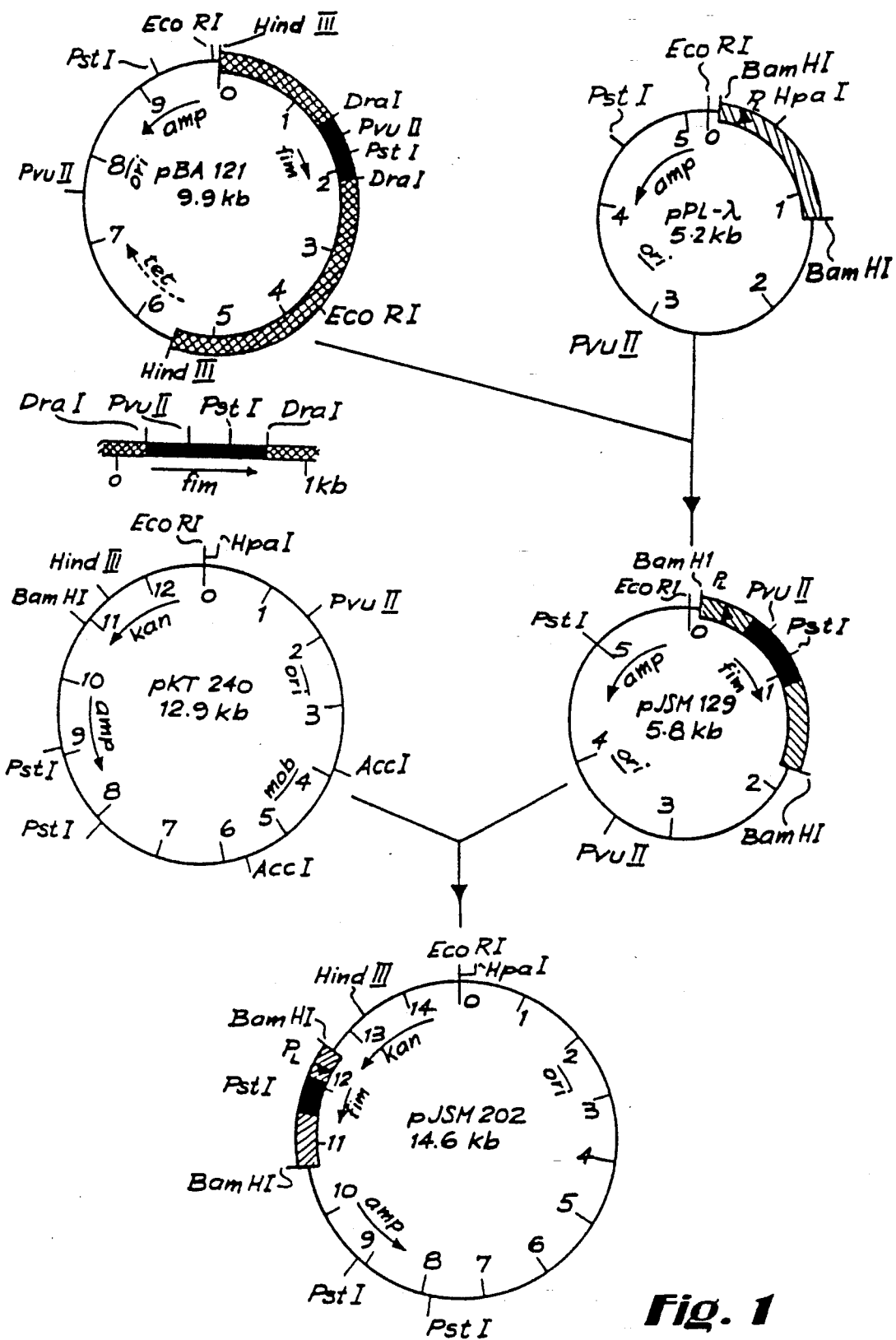
FIG. 1 shows the genealogy and construction of pJSM202. A full description is given in the text. The cross-hatched sequences in pBA121 indicate those originally cloned from B.nodosus VCS1001, with the internal dark segment delineating the Dra 1 fragment which contains the fimbrial subunit gene (see FIG. 2 for details). The hatched sequences in pPL-lambda indicate the Bam H1 segment (originally derived from bacteriophage lambda) which contains the $P_L$ promoter, and into which the Dra 1 fragment from pBA121 was cloned (at the Hpa 1 site). The exact orientation of this construction in pJSM202 was not determined (i.e. this segment may be reversed). The thin line in plasmids pBA121, pPL-lambda and pJSM129 represents sequences derived from pBR322. The thin line in pJSM202 represents sequences derived from pKT240. Various restriction endonuclease sites are indicated accordingly. The numbers refer to the distance in kilobases (kb) around each plasmid. The arrows indicate the direction of transcription and the approximate boundaries of the gene in question. Abbreviations are: fim, fimbrial subunit gene; amp, ampicillin (or carbenicillin) resistance; tet, tetracyline resistance (non-functional in pBA121); kan, kanamycin resistance; ori, origin of replication; mob, mobilization functions.

The *B.nodosus* fimbrial subunit gene used in this example was derived from *B.nodosus* VCS 1001, formerly known as strain 198 (ATCC No. 25549), which is the designated prototype strain of serogroup A (subtype 1). The gene is located on a 5.5 kb Hind III fragment of *B.nodosus* DNA which was originally isolated by immunological screening of a cloned Hind III genomic library constructed in *E.Coli* using the positive selection plasmid vector pTR262, as described in the applicants' copending Australian patent application No. 34979/84. The 5.5 kb Hind III segment was subsequently subcloned into the plasmid vector pBR322 to yield pBA121 (Anderson, B. J., et al., J. Bacteriol. 160, 748–754 (1984)). FIG. 1 shows the restriction map of this plasmid and the location of the structural gene encoding the fimbrial subunit. The nucleotide sequence of this gene and adjacent DNA has now been determined, and is presented in FIG. 2.

The *P.aeruginosa* host strain used in this example is *P.aeruginosa* strain PAK/2Pfs (ATCC No. 53308, deposited in The American Type Culture Collection, 12301 Parklawn Dr., Rockville, Md, 20852, on Oct. 30), which is a multifimbriate mutant of strain PAK. The vector plasmid used in this example is pKT240 (Bagdasarian, M. M., et al., Gene 26, 273-282 (1983) which is a broad host range plasmid, capable of being replicated and maintained in both *E.coli* and *P.aeruginosa,* and which contains genetic markers of penicillin (ampicillin, carbenicillin) and kanamycin resistance, as well as a number of unique restriction sites for gene cloning (see FIG. 1).

A. Genetic Constructions and Engineering

In the initial constructions, the 5.5 kb Hind III fragment containing the *B.nodosus* fimbrial subunit gene was subcloned directly into the Hind III site of pKT240 (see FIG. 1), to yield pJSM125, This plasmid was then transformed into competent *P.aeruginosa* PAK/2Pfs cells (as described below). Immunological analyses of the resulting transformants showed that the *B.nodosus* fimbrial subunit was expressed in these cells, but at a relatively low level. Nevertheless, there were clear indications that at least some of the *B.nodosus* fimbrial subunits produced in these recombinants were assembled into mature fimbriae, since the antigenic signal co-purified with the fimbriae and was retained in the most highly purified fractions. However, the signal was weak, and the vast majority of the fimbriae were composed of the endogenous Pseudomonas subunit normally produced by the host strain.

The problem of the low expression of the *B.nodosus* fimbrial subunit gene in *P.aeruginosa* was overcome by placing this gene under the transciptional control of the strong promoter, $P_L$, from bacteriophage lambda, as outlined in FIG. 1, and detailed below:

pBA121 was digested with the restriction endonuclease Dra I which cleaves at convenient sites flanking the fimbrial subunit gene, one 30 nucleotides upstream from the initiation codon (ATG), and the other 69 nucleotides downstream from the termination codon (TAA), to yield a blunt-ended 576 base-pair gene cartridge (see FIG. 2). This cartridge was purified by gel electrophoresis, and ligated into the (blunt-ended) Hpa 1 site located downstream from the $P_L$ promoter in the plasmid pPL-lambda (Pharmacia P-L Biochemicals), to yield PJSM 129 (FIG. 1). All constructions involving the $P_L$ promoter were carried out in *E.coli* strain E418 grown at 30° C. *E.coli* E418 is a lambda lysogen strain containing the temperature sensitive Cl857 repressor gene. The correct orientation of the Dra I insert with respect to the $P_L$ promoter in the plasmid was checked by reference to the internal Pvu II and Pst 1 sites within the fimbrial subunit gene, and verified by the overproduction of the antigen in *E.coli* after shifting the culture to 42° C. This construction is apparently lethal in *E.coli* cells which lack a functional Cl repressor, presumably because the cells are unable to cope with the large amount of *B.nodosus* fimbrial subunit being produced and deposited into the membrane.

The *B.nodosus* fimbrial gene/$P_L$ promoter construction was then transferred into the vector pKT240 as follows:- pJSM129 was digested with the restriction endonuclease Bam Hl to release a fragment of approximately 1.75 kb, which includes the $P_L$ promoter and the fimbrial subunit gene (see FIG. 1). This fragment was purified by gel electrophoresis and ligated into the corresponding site in pKT240, to yield the plasmid designated pJSM202 (ATCC No. 40203, deposited in the American Type Culture Collection, 12301 Parkview Drive, Rockville, Md., 20852, on Oct. 30, 1985).

The presence of the Bam Hl fragment in this plasmid was verified by restriction endonuclease analysis, although the orientation of this insert was not determined. Further characterization showed that *E.coli* E418 cells carrying pJSM202 produced large amounts of the *B.nodosus* fimbrial subunit when cultured at 42° C. (see FIG. 3), and that pJSM202, like pJSM129, does not generate viable transformants of *E.coli* strains lacking the Cl repressor. (In both cases, however, this ability may be restored by the insertion in the plasmids themselves of a cloned DNA segment containing the C1857 gene).

All constructions, manipulations and analyses described above were carried out using standard genetic engineering techniques.

B. Morphogenetic expression of *B.nodosus* fimbriae in *Pseudomonas aeruginosa* PAK/2Pfs (ATCC No. 53308) containing pJSM202 (ATCC No. 40203)

(i) Transformation of fimbriate *P.aeruginosa* with pJSM202

*P.aeruginosa* strain PAK/2Pfs was made competent for DNA transformation as follows: cells were grown overnight at 43° C. (to stationary phase) in $KNO_3$ broth (2.5% Oxoid Nutrient Broth No. 2, 0.5% yeast extract and 0.4% $KNO_3$). A sample of the culture was then diluted 1:25 with fresh $KNO_3$ broth and incubated with shaking at 37° C. until the culture reached the early mid-log phase of growth. The culture was then chilled quickly on ice, and the cells recovered by centrifugation. All subsequent steps were carried out at 4° C. The cells were washed twice by resuspension in one fifth volume of 0.1M $MgCl_2$, and re-centrifugation. The cells were then resuspended in one eighth volume of 0.15M $MgCl_2$ and left on ice for 20–30 minutes. The cells were again recovered by centrifugation and finally resuspended in one twentieth volume of 0.15M $MgCl_2$, and kept on ice ready for transformation.

pJSM202 was transformed into competent P.aeruginosa PAK/2Pfs cells as follows: approximately 200-400 ng of purified plasmid DNA (in 5-10 ul of buffer) was added to 0.2 ml of cell suspension, mixed, and placed on ice for one hour. The transformation mixture was then subjected to heat shock at 42° C. for 2 minutes, then diluted with an equal volume of $KNO_3$ broth, and incubated at 37° C. for one hour to allow phenotypic expression of antibiotic resistance genes on the plasmid. Samples (0.1 ml) were then plated onto nutrient (Luria broth) plates containing carbenicillin (1 mg/ml). (P.aeruginosa PAK/2Pfs is not particularly sensitive to ampicillin or kanamycin). Plates were incubated at 37° C. and visible colonies appeared in about 2 days.

Several transformants were selected and all verified to contain pJSM202 by plasmid isolation and restriction analysis. This plasmid is therefore not lethal for P.aeruginosa PAK/2Pfs (or other fimbriate strains tested), despite the fact that we found that the $P_L$ promoter is highly active in these cells and that large amounts of the B.nodosus fimbrial subunit are produced. However, the transformants were found to grow relatively slowly, and to have a short storage life as plate cultures, which necessitated regular subculture to maintain viability. These transformants also do not appear to store well in standard frozen conditions (as suspensions in nutrient broth containing 15% glycerol at $-70°$ C.). For this reason, we periodically regenerated fresh stocks by re-transformation of P.aeruginosa PAK/2Pfs with pJSM202. These recombinant transformed cells are (generically) designated PKN-A1.

(ii) Isolation and analysis of fimbriae produced by P.aeruginosa PKN-A1 (PAK/2Pfs+pJSM202)

Examination of P.aeruginosa PKN-A1 cells has shown that not only are large amounts of the B.nodosus fimbrial subunit produced in these cells, but also that the fimbrial strands extruded by these cells are actually composed entirely, or almost entirely, of this protein, with little or no P.aeruginosa-type subunits present.

The morphogenetic expression of B.nodosus fimbriae in PKN-A1 has been demonstrated by fimbrial isolation and purification, in conjunction with electrophoretic, immunological and electron micrographic analyses, alone or in combination, as described below. Although B.nodosus-type fimbriae are physically very similar to those naturally produced by the P.aeruginosa host strain, they may be distinguished using specific antisera. Furthermore, the fimbrial subunits from the donor B.nodosus strain VCS 1001 and the host P.aeruginosa strain PAK/2Pfs have slightly different molecular weights and thus may also be distinguished by their electrophoretic mobilities in SDS-polyacrylamide gels (see FIGS. 4, 5 and 6); the apparent molecular weight of the B.nodosus VSC 1001 subunit is approximately 17,000, whereas that of the P.aeruginosa PAK/2Pfs subunit is approximately 16,000; the actual molecular weights (calculated from sequence) are 16,218 (151 amino-acids) and 15,082 (145 amino-acids), respectively.

For the analyses described below, the bacterial cells were cultured on solid media; the host P.aeruginosa strain PAK/2Pfs on nutrient (Luria broth) agar; the recombinant P.aeruginosa strain PKN-A1 (containing pJSM202) on the same medium supplemented with 1 mg carbenicillin/ml; recombinant E.Coli E418 containing pJSM202 on the same medium supplemented with 50 ug ampicillin/ml; and B.nodosus cells on "hoof" agar (as described by Mattick et al (1984). J. Bacteriol 160, 740-747). Cultures were harvested by scraping into phosphate-buffered saline.

Morphogenetic expression of B.nodosus-type fimbriae in P.aeruginosa PKN-A1 cells was first indicated by the presence of substantial amounts of this antigen in the extracellular environment. In many fimbriate bacteria, including B.nodosus and P.aeruginosa, a proportion of the fimbriae appear to be shed into the medium (or resuspension buffer) and remain there after removal of the cells by centrifugation. Additional fimbriae may be removed by mechanical blending of the cell suspension (see FIG. 4), or by heating the culture (to about 600° C.) for a brief period. This is illustrated in FIG. 3, which shows a Western Transfer (immunoblot) analysis of the cell pellet and derived supernatant fractions from recombinant cells. The results show firstly that the B.nodosus fimbrial subunit is transcribed very actively from the $P_L$ promoter in P.aeruginosa cells containing pJSM202, at a level at least two orders of magnitude higher than that in the same host containing pJSM125, wherein the gene is transcribed from an associated promoter within the original cloned segment of B.nodosus DNA. Secondly, a large proportion of the fimbrial subunit antigen is found in the supernatant fraction obtained from P.aeruginosa PKN-A1. This may be contrasted with the situation in E.Coli E418 cells containing pJSM202, where the antigen is entirely located in the cell (pellet) fraction (the traces found in the supernatant are apparently derived from cell fragments not removed by centrifugation). A substantial amount of B.nodosus fimbrial subunit is also found with the cells in the case of PKN-A1, but it is not known to what extent this represents fimbriae not dislodged from the cell, or (as yet) unassembled subunits accumulated within the cell. Thirdly, the size of the fimbrial subunit found in E.coli is in fact slightly larger than that found in P.aeruginosa or in B.nodosus itself. This appears to be due to the inability of E.coli to cleave the short signal peptide from the primary translation product (see Table 1), which is presumably part of the normal process of morphogenetic expression.

The assembly of B.nodosus fimbrial subunits into mature fimbriae in P.aeruginosa PKN-A1 cells was also demonstrated by the presence of this antigen in purified fimbriae isolated under different conditions. Fimbriae may be recovered from cell-free supernatants by either one of the independent methods of isoelectric precipitation at pH 4.5 or precipitation induced by the addition of $mgcl_2$. These are standard procedures applicable to the isolation of fimbriae from both P.aeruginosa and B.nodosus. Using either method, good yields of purified fimbriae (approximately 1 to 1.5 mg per standard (85 mm) Petri dish culture) were obtained from the recombinant PKN-A1 cells, which was confirmed by electron microscopy of negatively-stained samples. These fimbriae could also be further purified by isopycnic banding in CsCl gradients. Electrophoretic analysis (FIG. 4) showed that the fimbriae isolated from PKN-A1 cells are comprised primarily of a structural subunit which co-migrates in the gel with that obtained from B.nodosus. Somewhat unexpectedly, there is little or no evidence of the fimbrial subunit characteristic of the host strain PAK/2Pfs (see FIG. 4; also below).

Figure 5:
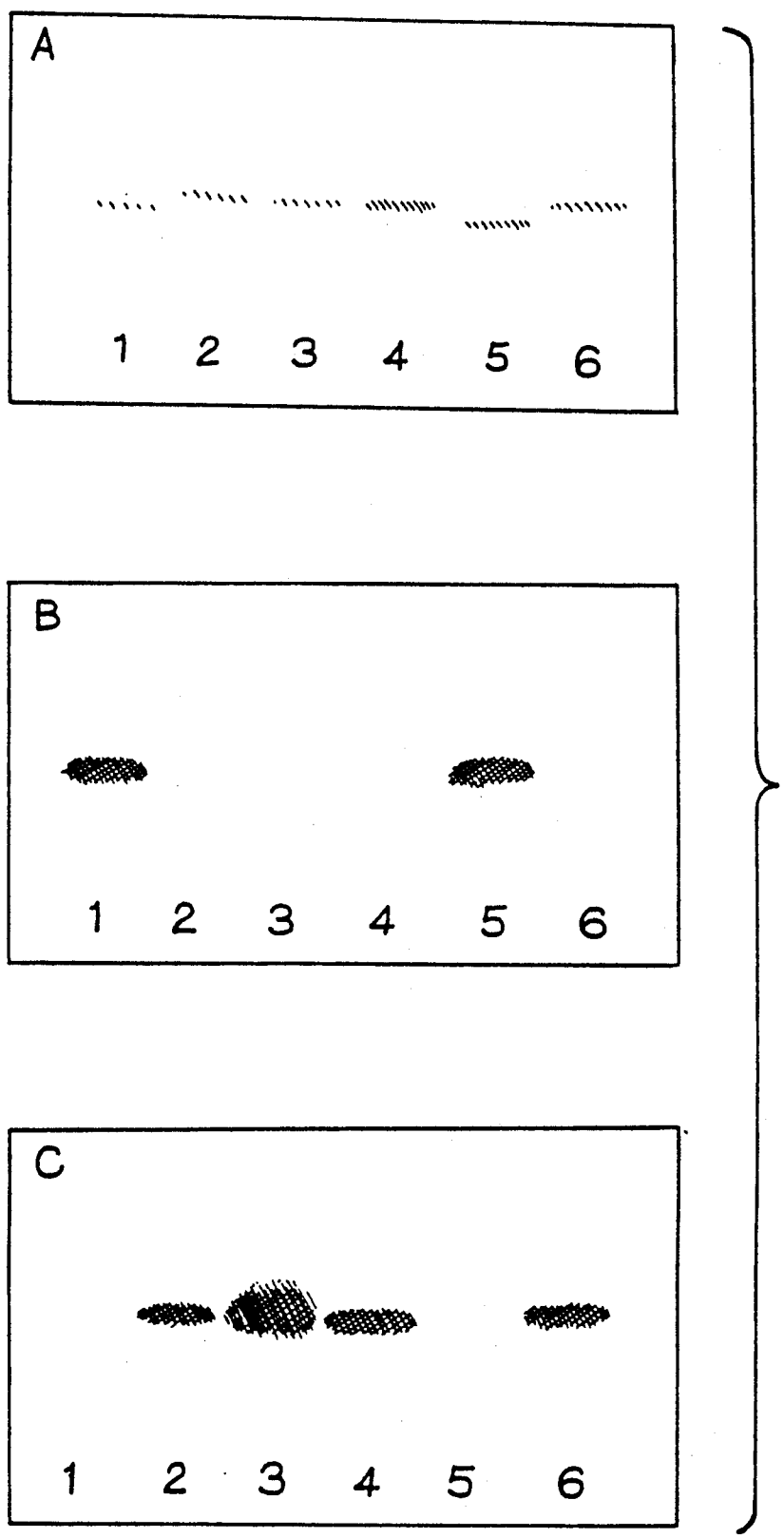
FIG. 5 shows the electrophoretic and immunological characteristics of fimbriae purified from P.aeruginosa PKN-Al. Fimbriae were purified (by two rounds of isoelectric precipitation) from two independent primary clones of P.aeruginosa PAK/2Pfs transformed with pJSM202 (Lanes 3 and 4), and compared with fimbriae obtained from the host P.aeruginosa strain PAK/2Pfs (Lanes 1 and 5) and from B.nodosus VCS 1001 (Lanes 2 and 6). These fimbriae (about 2 ug in each case) were displayed on SDS-polyacrylamide gels, as described in the legend to FIG. 3, and stained with Coomassie Blue R250 (Panel A). Similar (unstained) displays were subjected to Western transfer analysis, as described in the legend to FIG. 3, using either anti-P.aeruginosa PAK/2Pfs fimbrial antiserum (panel B) or anti-B.nodosus fimbrial antiserum (panel C). Only the lower portion of the gel (containing the fimbrial subunit) is shown.
Figure 6:
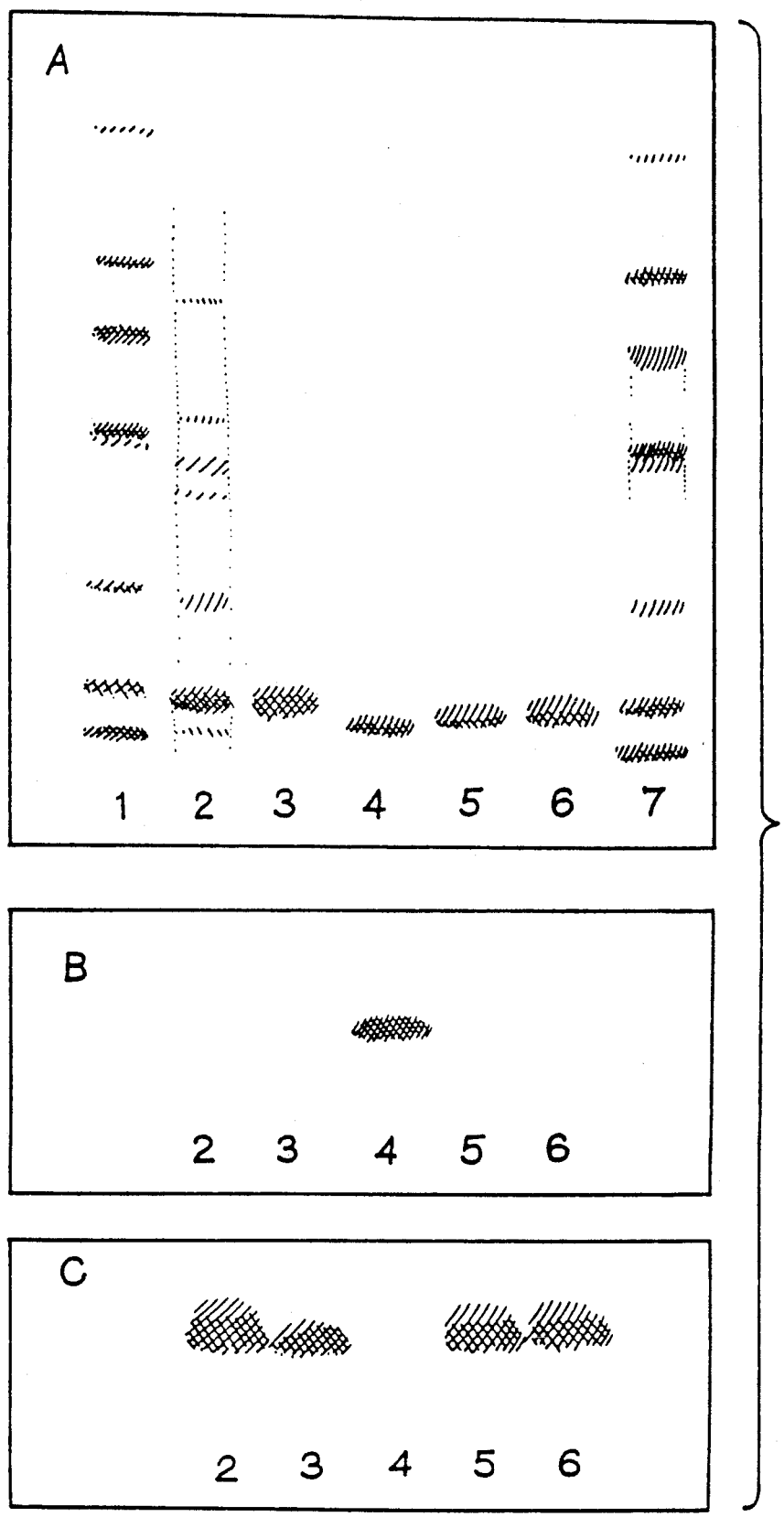
FIG. 6 shows the electrophoretic and immunological analysis of the antigen samples used in the vaccination trial. Lane 2 contains whole cells of B.nodosus VCS 1001; lane 3 contains fimbriae purified from B.nodosus VCS 1001; lane 4 contains fimbriae purified from P.aeruginosa PAK/2Pfs; lane 5 contains fimbrae purified from P.aeruginosa PKN-Al; lane 6 contains fimbriae purified (using $MgCl_2$) from P.aeruginosa PKN-Al (see text for details). Lanes 1 and 7 contain a mixture of standard protein molecular weight markers. Samples were displayed by electrophoresis on SDS-polyacrylamide gels and either stained with Coomassie Blue R250 (panel A) or subjected to Western transfer analysis using anti-P.aeruginosa PAK/2Pfs fimbrial antiserum (panel B) or anti-B.nodosus VCS 1001 fimbrial antiserum (panel C), as described in the legends to FIGS. 3 and 5. The entire gel display is shown in panel A, whereas only the lower portion containing the fimbrial subunits is shown in panels B and C.

These results were confirmed by Western transfer analysis of the fimbriae produced by the PKN-Al cells, compared with those obtained from *B.nodosus* strain VCS 1001 and *P.aeruginosa* PAK/2Pfs (FIG. 5). This experiment clearly shows that not only do the fimbriae produced by PKN-Al consist of a structural subunit which has the same electrophoretic mobility as that found in *B.nodosus* itself (FIG. 5A), but also that this protein is recognised by antibodies directed against *B.nodosus* fimbriae (FIG. 5C). The reciprocal Western, using anti-*P.aeruginosa* fimbrial antiserum, confirms that the fimbriae produced by these recombinant cells contain little, if any, of the structural subunit naturally expressed by the host (FIG. 5B). Control experiments have shown that the presence of the vector plasmid pKT240 by itself does not affect the composition of the fimbriae in *P.aeruginosa.*

The production of *B.nodosus*-type fimbriae in PKN-Al cells was also independently verified by immune-gold labelling and electron micrographical examination. Fimbriae were prepared from *B.nodosus* VCS 1001, *P.aeruginosa* strain PAK/2Pfs and *P.aeruginosa* PKN-Al, placed on grids and incubated with either anti-*P.aeruginosa* PAK/2Pfs fimbrial antiserum or anti-*B.nodosus* VCS 1001 fimbrial antiserum. After washing the samples were incubated with gold-labelled Protein A, washed again, then negatively stained and visualized by electron microscopy. Antibody binding was indicated by the presence of electron-dense spherical gold particles, as well as by the clumping together of the fimbrial strands. As expected, *B.nodosus* VCS 1001 fimbriae reacted strongly with the homologous antiserum, but not with antiserum raised against *P.aeruginosa* fimbriae. The reverse was also true, in that *P.aeruginosa* PAK/2Pfs reacted strongly with the homologous antiserum, but not with antiserum against *B.nodosus* fimbriae. The pattern is entirely reversed in the recombinant *P.aeruginosa* cells containing pJSM202, which now have a similar profile to that observed in *B.nodosus.* Fimbriae produced by PKN-Al are not recognized by antibodies directed against *P.aeruginosa* fimbriae, but rather react strongly with those against *B.nodosus* fimbriae. These results may be summarized in the following table, with + indicating antibody recognition and − the absence of antibody recognition.

| | Strain | | |
|---|---|---|---|
| | *B. nodosus* | *P. aeruginosa* | |
| Antiserum | VCS 1001 (Donor) | PAK/2Pfs (Host) | PKN-Al (Recombinant) |
| Anti-*B. nodosus* VCS 1001 fimbriae | + | − | + |
| Anti-*P. aeruginosa* PAK/2Pfs fimbriae | − | + | − |

Several other criteria were also used to verify the production of *B.nodosus* fimbriae by *P.aeruginosa* cells containing pJSM202. These include demonstrations that antisera raised against the recombinant fimbriae will agglutinate *B.nodosus* (VCS 1001) cells (see vaccination trial below), and reciprocally that antisera raised against *B.nodosus* (VCS 1001) will cause agglutination of the recombinant *P.aeruginosa* PKN-Al cells. These agglutination reactions are (*B.nodosus*) serotype-specific. Control experiments showed that anti-*B.nodosus* antisera will not agglutinate the host *P.aeruginosa* PAK/2Pfs (with or without the vector plasmid PKT240), and that antisera raised against normal *P.aeruginosa* fimbriae will not agglutinate *B.nodosus.* Similar results have been obtained in standard solid-phase antibody-antigen binding assays,, such as ELISA tests.

These results demonstrate that *P.aeruginosa* PKN-Al cells containing the recombinant plasmid pJSM202 produce mature fimbrial structures which are physically, structurally and antigenically indistinguishable from those produced by the *B.nodosus* strain from which the fimbrial subunit gene was originally derived. As we shall subsequently demonstrate, these recombinant-produced fimbriae are also equally effective in inducing protective immunity against footrot.

Similar results have been obtained using other fimbriate *P.aeruginosa* strains as the host cell for the recombinant plasmid pJSM202. These include *P.aeruginosa* PAK (ATCC 25102) the parent of PAK/2Pfs, as well as *P.aeruginosa* PA01 (ATCC 25247), and its derived multifimbriate mutant DB-2, which normally express a structurally and serologically distinct form of fimbrial subunit from that found in PAK strains.

The insertion of pJSM202 into fimbriate *P.aeruginosa* has effectively resulted in the complete substitution of the *B.nodosus* fimbrial subunit for that normally produced by the cells. The fact that the fimbriae produced by these recombinants contain little or no endogenous *P.aeruginosa* structural subunits suggests that the high level of expression of the *B.nodosus* subunit has either prevented the entry of the endogenous subunit into the assembly pathway or has resulted in feedback inhibition (presumably via common signals in the conserved region) of the synthesis of the endogenous subunit, either at the transcriptional or translational level. In either caser the provision of a strong promoter to increase the expression of the cloned *B.nodosus* fimbrial subunit gene in the *P.aeruginosa* host cell is clearly an important feature of the invention. However, the exact nature of the promoter employed does not appear to be critical. We have obtained similar results using alternative constructions wherein the fimbrial subunit gene is under the transcriptional control of the strong $P_R$ promoter from bacteriophage lambda. The expression of the fimbrial subunit gene from either the $P_L$ or $P_R$ promoter may be regulated by the insertion into the plasmid of a cloned copy of the C1857 repressor gene, which reduces selective pressure against the plasmid during normal maintenance of transformed cells. It is also possible to consider the use of other strong promoters, such as tac, which may be induced by chemical signals rather than temperature shift.

The results presented herein substantiate our prediction that Type 4 fimbrial subunits from different bacterial species do share common topogenic signals for fimbrial morphogenesis, and may be interchanged among compatible hosts. This is certainly the case for *B.nodosus* and *P.aeruginosa,* and should be equally applicable to other Type 4 species retaining the conserved hydrophobic amino-terminal region of the fimbrial subunit. Further, since variation in the carboxy-terminal region of this protein does not appear to interfere with the process of fimbrial assembly, it is also feasible that the co-cloning of two or more genes encoding related Type 4 fimbrial subunits within the same compatible host cell would result in the formation of mixed or hybrid fimbriae (consisting of a random array of the input subunits), which may then provide a multivalent antigenic preparation active against more than one serotype, or even perhaps against more than one species.

There are several other modifications of the basic system which may be considered in particular circumstances. For example, in some cases it may be desirable to eliminate the expression of the endogenous fimbrial subunit produced by the host cell. This may be achieved by a variety of methods, including traditional mutant selection, transposon mutagenesis, or in vitro modification of the gene followed by recombinational insertion in vivo. The system may also be improved by modification of (the expression of) genes involved in the fimbrial assembly process. Adjustments may also be made within the conserved amino-terminal sequence of the fimbrial subunit itself to improve the efficiency of fimbrial assembly in a heterologous Type 4 species. This may be accomplished by gene fusions, or site-directed mutagenesis in vitro using synthetic oligonucleotides to alter specific amino-acid codons, so that the consensus sequence is brought into close alignment with that normally operative in, and recognized by, the preferred host.

It will be recognized by persons skilled in the art that numerous other variations and modifications can be made to the invention as described above without departing from the spirit or scope of the invention as broadly described.

C. Vaccination Trial

The efficacy of the fimbriae produced by the recombinant P.aeruginosa PKN-Al cells in inducing protective immunity against footrot infection in sheep was tested in a vaccination trial. The vaccination trial was conducted as follows: a total of 73 naive sheep were randomly distributed among 7 groups, containing either 10 or 11 individuals per group. Two groups were assigned as negative controls—one received no treatment (Group 1) and the other was vaccinated with isolated fimbriae from the host P.aeruginosa strain PAK/2Pfs (Group 4). There were also two positive control groups, vaccinated with either whole cells (Group 2) or isolated fimbriae (Group 3) from B.nodosus VCS 1001. Two experimental groups (Groups 5 and 6) were vaccinated with different amounts of fimbriae isolated from the recombinant P.aeruginosa strain PKN-Al (containing pJSM202). A third experimental group (Group 7) was also vaccinated with fimbriae from PKN-Al, in this case isolated by an alternative procedure (see below).

| Group | Vaccine Antigen | Dose |
|---|---|---|
| 1 | — | — |
| 2 | Whole cells B. nodosus VCS 1001 | 5 × 10⁹ cells |

-continued

| Group | Vaccine Antigen | Dose |
|---|---|---|
| 3 | Isolated fimbriae B. nodosus VCS 1001 | 250 ug |
| 4 | Isolated fimbriae PAK/2Pfs | 250 ug |
| 5 | Isolated fimbriae PKN-Al | 250 ug |
| 6 | Isolated fimbriae PKN-Al | 500 ug |
| 7 | Isolated fimbriae PKN-Al (MgCl$_2$) | 250 ug |

Cells were grown on agar plates and harvested by scraping into sterile phosphate-buffered saline (PBS). For fimbrial isolation, these cell suspensions were subjected to mechanical blending and the cells then removed by centrifugation. Fimbriae were recovered from the cell-free supernatant by isoelectric precipitation with 0.1M Na acetate (pH 4.5) or, in the case of Group 7, by precipitation with 0.1M MgCl$_2$. The fimbriae were then redissolved in sterile PBS, and purified by a further round of precipitation, by the method originally employed. The contents and purity of each of the antigen preparations used in the vaccination trial were then checked by electrophoretic display and Western transfer analysis, using anti-B.nodosus VCS 1001 and anti-P.aeruginosa PAK/2Pfs antisera (Table 7).

Vaccines were prepared using a standard alum/oil adjuvant system: An appropriate amount of antigen was resuspended in sterile PBS, to which one-seventh volume of 10% potash alum (ALK(SO$_4$)$_2$) was added, and the pH adjusted to 6.2. One hundredth volume of Tween 80 was added, and the mixture emulsified with an equal volume of Freunds Incomplete Adjuvant. Each individual dose was presented in a volume of 2ml, and contained the amount of antigen specified in the table above. Each animal received two doses—a primary vaccination, followed by a booster shot 28 days later. Four days after boosting, the animals were predisposed to challenge by standing in pens in damp conditions (on wet mats). Challenge was artificially administered three days later (i.e. one week after boost) by applying cultured cells of B.nodosus VCS 1001 to each foot. Animals from all groups were penned together for the duration of the trial. Blood samples were taken throughout the trial to monitor the serum agglutinating titre against B.nodosus VCS 1001. The presence and severity of infection was assessed 21 days after challenge by examining each individual foot for lesions. The data are summarized in Table 2.

TABLE 2

| GROUP | 1 | 2 | 3 | 4 | 5 | 6 | 7 |
|---|---|---|---|---|---|---|---|
| Vaccine | Nil | B. nodosus cells (5 × 10⁹) | B. nodosus fimbriae 250 ug | P. aeruginosa fimbriae 250 ug | PKN-Al fimbriae 250 ug | PKN-Al fimbriae 500 ug | PKN-Al fimbriae MgCl$_2$ 250 ug |
| Affected sheep | 10/10 | 5/11 | 7/10 | 11/11 | 5/11 | 4/10 | 4/10 |
| Severe (underrunning) Lesions | 25/40 | 7/44 | 6/40 | 29/44 | 9/44 | 6/40 | 8/40 |
| (% feet) | (63%) | (16%) | (15%) | (66%) | (20%) | (15%) | (20%) |
| G.M.F.S. Agglutinin Titre | 2.2 | 0.7 | 1.1 | 2.5 | 1.0 | 0.75 | 0.9 |
| +2 wk | N.D. | 10,900 | 7,200 | N.D. | 11,600 | 12,600 | 6,800 |
| +3 wk | 200 | 7,000 | 3,400 | 200 | 8,000 | 6,800 | 3,200 |

Legend Table 2: Affected animals are those defined as having at least one foot with a lesion score of 3 or 4, or at least two feet with a lesion score of 2, at 3 weeks after challenge. The lesion score was assessed on a standard scale of 2 to 4 as follows: 2, obvious interdigital dermatitis; 3, underrunning lesions of the soft horn of the heel of the hoof; and 4, underrunning lesions of the hard horn of the hoof. (A lesion score of 1 is normally applied to feet exhibiting symptoms of mild interdigital dermatitis. This may be due to other causes, and hence was not considered in the assessment). Severe lesions are those underrunning the hoof i.e. a score of either 3 or 4. G.M.F.S. is the group mean foot score, and was calculated by as the sum of the lesion scores for all feet of all animals in the group, divided by the number of feet in the group. The agglutinating titre was measured as the reciprocal of the maximum dilution at which visible K-agglutination of B.nodosus (VCS 1001) cells was observed. Two-fold serial dilutions were performed. The data is presented for samples taken at 2 weeks and 3 weeks after challenge (i.e. 3 and 4 weeks after boost). The data is expressed as the geometric mean value for the group (rounded off to the nearest 100). N.D.=not determined.

The results of the vaccination trial clearly demonstrate that the recombinant fimbriae confer the same level of protection as B.nodosus whole cells or fimbriae against homologous footrot challenge. There is no significant difference between either the serum agglutinating titres or the level of protective immunity observed in groups vaccinated with either the natural or recombinant material. Complete immunity against footrot challenge is rarely observed in such vaccination trials, especially when a highly virulent strain such as VCS 1001 is involved. The response of individual animals to vaccination is quite variable. However, although neither the natural nor recombinant material conferred full immunity against footrot infection in this trial, there is a large and, in practical terms, important difference between the vaccinated groups and negative controls. All animals in the negative control groups (i.e. either untreated or Yaccinated with normal P.aeruginosa fimbriae) became affected with severe footrot, with about 65% of all feet having underrunning lesions. The average lesion score for these groups was 2.4. Such lesions are relatively rare in the groups vaccinated with B.nodosus cells or fimbriae, or fimbriae produced by recombinant cells, severe symptoms being observed in only 15-20% of all feet. The average lesion score among these groups was only 0.9. This effectively means the difference between sheep which are debilitated by the disease, and those which are only mildly affected and inconvenienced, albeit with some exceptions. This practical difference is important in the field situation.

The claims defining the invention are as follows:

1. A method for the production of an antigenic preparation for use in raising antibodies active against a species of bacteria naturally producing Type 4 fimbriae, said method comprising the steps of:
   culturing genetically engineered Pseudomonas aeruginosa host cells, containing the genes encoding the fimbrial structural subunit antigens of at least one strain of the said species of bacteria, and an endogenous compatible system for the morphogenetic assembly of Type 4 fimbriae, said host cells being such that mature fimbriae are produced as extracellular structures; and
   harvesting the whole or a part of the fimbriae substantially free of the host cells.

2. A method for the production of an antigenic preparation as claimed in claim 1 in which the genes encoding the fimbrial structural subunit antigens are from a species selected from the group consisting of B. nodosus and M. bovis.

3. A method for the production of an antigenic preparation as claimed in claim 1 in which the genes encoding the fimbrial structural subunit antigens are derived from a species selected from the group consisting of N. gonorrhoeae, N. meningitidis and M. nonliquefaciens.

4. A method for the production of an antigenic preparation as claimed in claim 1 or 2 in which the genetically engineered Pseudomonas aeruginosa host cells contain genes for a plurality of fimbrial structural subunit antigens, said genes being from different species or genera.

5. A method for the production of an antigenic preparation as claimed in claim 1 or 2 in which the genetically engineered Pseudomonas aeruginosa host cells contain genes for a plurality of fimbrial structural subunit antigens, said genes being from different serotypes of a single species of bacteria.

6. A method for the production of an antigenic preparation as claimed in claim 1 in which the mature fimbriae or fragments thereof are of at least one serotype of B. nodosus.

7. A method for the production of an antigenic preparation as claimed in claim 1 in which the genetically engineered Pseudomonas aeruginosa is derived from Pseudomonas aeruginosa Pak/2Pfs (ATCC No. 53308).

8. A method for the production of an antigenic preparation as claimed in claim 1 in which the gene encoding the fimbrial structural subunit antigen is under the transcriptional control of a strong promoter operative in the selected host.

9. A method for the production of an antigenic preparation as claimed in claim 8 in which the strong promoter is regulatable.

10. A method for the production of an antigenic preparation as claimed in claim 8 in which the promoter is the $P_L$ or $P_R$ promoter derived from the bacteriophage lambda.

11. A method for the production of an antigenic preparation as claimed in claim 1 in which the gene encoding the fimbrial structural subunit antigen is contained within a plasmid.

12. A method for the production of an antigenic preparation as claimed in claim 11 in which the plasmid is plasmid pJSM202 (ATCC No. 40203).

13. A method for the production of an antigenic preparation as claimed in claim 1 in which the gene encoding the fimbrial structural subunit antigen is inserted within the host bacterial cell chromosome.

14. A genetically engineered Pseudomonas aeruginosa, said Pseudomonas aeruginosa containing exogenous genes encoding the fimbrial structural subunit antigens of at least one strain of bacteria which naturally produces Type 4 fimbriae such that expression of the exogenous genes results in the production of fimbriae of the least one strain as extracellular structures.

15. A genetically engineered Pseudomonas aeruginosa as claimed in claim 14 in which the exogenous genes are derived from B nodosus or M. boxis.

16. a genetically engineered Pseudomonas aeruginosa as claimed in claim 14 in which the exogenous genes are derived from a species selected from the group consisting of N. gonorrhaeae, N. meningitidis and M. nonliquefaciens.

17. A genetically engineered Pseudomonas aeruginosa as claimed in claim 14 in which the exogenous genes are derived from a different species or genera.

18. a genetically engineered *Pseudomonas aeruginosa* as claimed in claim 14 in which the exogenous genese encode fimbrial structural subunit antigens of different serotypes of a single species or bacteria.

19. A genetically engineered *Pseudomonas aeruginosa* as claimed in claim 14 in which the exogenous genes are derived from at least one serotype of *B. nodosus*.

20. a genetically engineered *Pseudomonas aeruginosa* as claimed in claim 14 in which the exogenous genes are under the transcriptional control of a strong promoter operative in the genetically engineered bacteria.

21. A genetically engineered *Pseudomonas aeruginosa* as claimed in claim 20 in which the strong promoter is regulatable.

22. A genetically engineered *Pseudomonas aeruginosa* as claimed in claim 20 in which the promoter is the $P_L$ or $P_R$.

23. A genetically engineered *Pseudomonas aeruginosa* as claimed in claim 14 in which exogenous genes are contained within a plasmid.

24. A genetically engineered *Pseudomonas aeruginosa* as claimed in claim 23 in which the plasmid is plasmid pJSM202 (ATCC No. 40203).

25. A genetically engineered *Pseudomonas aeruginosa* as claimed in claim 14 in which the exogenous genes are inserted within the genetically engineered bacteria's chromosome.

26. *Pseudomonas aeruginosa* PAK/2fs (ATCC No. 53308) transformed with plasmid pJSM202 (ATCC No. 40203).